(12) United States Patent
Schwartz et al.

(10) Patent No.: US 8,403,943 B2
(45) Date of Patent: Mar. 26, 2013

(54) INSERTION SYSTEM FOR IMPLANTING A MEDICAL DEVICE AND SURGICAL METHODS

(75) Inventors: Herbert Eugene Schwartz, Fort Wayne, IN (US); Francis S. Proch, Huntertown, IN (US)

(73) Assignee: Howmedica Osteonics Corp., Mahwah, NJ (US)

( * ) Notice: Subject to any disclaimer, the term of this patent is extended or adjusted under 35 U.S.C. 154(b) by 747 days.

(21) Appl. No.: 12/310,057

(22) PCT Filed: Aug. 6, 2007

(86) PCT No.: PCT/US2007/075237
§ 371 (c)(1),
(2), (4) Date: Oct. 20, 2009

(87) PCT Pub. No.: WO2008/021771
PCT Pub. Date: Feb. 21, 2008

(65) Prior Publication Data
US 2010/0049220 A1 Feb. 25, 2010

Related U.S. Application Data

(60) Provisional application No. 60/821,593, filed on Aug. 7, 2006.

(51) Int. Cl.
*A61B 17/10* (2006.01)
(52) U.S. Cl. .................................................... 606/139
(58) Field of Classification Search ............... 606/139, 606/232, 144–151; 600/437, 471
See application file for complete search history.

(56) References Cited

U.S. PATENT DOCUMENTS 4,484,570 A 11/1984 Sutter et al.
(Continued)

FOREIGN PATENT DOCUMENTS

| CA | 1292596 | 12/1991 |
| CA | 2155422 | 8/1994 |

(Continued)

OTHER PUBLICATIONS

Adams et at., J. of Knee Surgery, Tissue Engineering for Meniscus Repair, vol. 18(1), 2005, pp. 25-30.
(Continued)

*Primary Examiner* — Corrine M McDermott
*Assistant Examiner* — Gregory Anderson
(74) *Attorney, Agent, or Firm* — Lerner, David, Littenberg, Krumholz & Mentlik, LLP

(57) ABSTRACT

The present invention relates to an insertion system for medical devices and to surgical methods for the implantation of the same. In one embodiment, the implantation system includes a guide wire and an insertion tool. The insertion tool includes a longitudinal bore extending therethrough for receipt of the guide wire. A portion of the longitudinal bore of the insertion tool mates with the outer surface of the guide wire to rotationally lock the insertion tool and the guide wire. Additionally, the medical device to be inserted includes a longitudinal bore for receipt of the guide wire. Similarly, at least a portion of the longitudinal bore of the medical device may also mate with the outer surface of the guide wire to rotationally lock the medical device and the guide wire. The rotational locks allow for rotation of the insertion tool to result in corresponding rotation of the medical device via rotation of the guide wire. In another embodiment, the insertion system further includes a needle having an eyelet for receiving and positioning filaments attached to the medical device.

14 Claims, 4 Drawing Sheets

U.S. PATENT DOCUMENTS

| | | |
|---|---|---|
| 4,884,572 A | 12/1989 | Bays et al. |
| 4,968,317 A | 11/1990 | Tormala et al. |
| 4,976,715 A | 12/1990 | Bays et al. |
| 5,041,129 A | 8/1991 | Hayhurst et al. |
| 5,059,206 A | 10/1991 | Winters |
| 5,085,629 A | 2/1992 | Goldberg et al. |
| 5,129,906 A | 7/1992 | Ross et al. |
| 5,152,791 A | 10/1992 | Hakamatsuka et al. |
| 5,236,431 A | 8/1993 | Gogolewski et al. |
| 5,261,914 A | 11/1993 | Warren |
| 5,269,809 A | 12/1993 | Hayhurst et al. |
| 5,370,662 A | 12/1994 | Stone et al. |
| 5,374,268 A | 12/1994 | Sander |
| 5,470,337 A | 11/1995 | Moss |
| 5,500,000 A | 3/1996 | Feagin et al. |
| 5,503,634 A | 4/1996 | Christy |
| 5,522,843 A | 6/1996 | Zang |
| 5,569,252 A | 10/1996 | Justin et al. |
| 5,669,909 A | 9/1997 | Zdeblick et al. |
| 5,681,353 A | 10/1997 | Li et al. |
| 5,683,366 A | 11/1997 | Eggers et al. |
| 5,702,462 A | 12/1997 | Oberlander |
| 5,725,549 A | 3/1998 | Lam |
| 5,730,744 A | 3/1998 | Justin et al. |
| 5,824,011 A | 10/1998 | Stone et al. |
| 5,842,477 A | 12/1998 | Naughton et al. |
| 5,871,475 A | 2/1999 | Frassica |
| 5,873,855 A | 2/1999 | Eggers et al. |
| 5,899,917 A | 5/1999 | Edwards et al. |
| 5,935,119 A | 8/1999 | Guy et al. |
| 5,954,747 A | 9/1999 | Clark |
| 5,976,127 A | 11/1999 | Lax |
| 5,980,559 A | 11/1999 | Bonutti |
| 6,039,753 A | 3/2000 | Meislin |
| 6,056,778 A | 5/2000 | Grafton et al. |
| 6,068,648 A | 5/2000 | Cole et al. |
| 6,096,060 A | 8/2000 | Fitts et al. |
| 6,102,046 A | 8/2000 | Weinstein et al. |
| 6,146,387 A | 11/2000 | Trott et al. |
| 6,203,556 B1 | 3/2001 | Evans et al. |
| 6,290,728 B1 | 9/2001 | Phelps et al. |
| 6,306,156 B1 | 10/2001 | Clark |
| 6,306,159 B1 | 10/2001 | Schwartz et al. |
| 6,319,270 B1 | 11/2001 | Grafton et al. |
| 6,319,271 B1 | 11/2001 | Schwartz et al. |
| 6,338,739 B1 | 1/2002 | Datta et al. |
| 6,387,111 B1 | 5/2002 | Barber |
| 6,468,277 B1 | 10/2002 | Justin et al. |
| 6,503,251 B1 | 1/2003 | Shadduck |
| 6,511,958 B1 | 1/2003 | Atkinson et al. |
| 6,514,514 B1 | 2/2003 | Atkinson et al. |
| 6,517,542 B1 | 2/2003 | Papay et al. |
| 6,548,569 B1 | 4/2003 | Williams et al. |
| 6,569,191 B1 | 5/2003 | Hogan |
| 6,595,990 B1 | 7/2003 | Weinstein et al. |
| 6,638,237 B1 | 10/2003 | Guiles et al. |
| 6,660,008 B1 | 12/2003 | Foerster et al. |
| 6,685,695 B2 | 2/2004 | Ferree |
| 6,685,728 B2 | 2/2004 | Sinnott et al. |
| 6,692,499 B2 | 2/2004 | Tormala et al. |
| 6,695,499 B2 | 2/2004 | Bartolome et al. |
| 6,763,836 B2 | 7/2004 | Tasto et al. |
| 6,780,164 B2 | 8/2004 | Bergheim et al. |
| 6,838,493 B2 | 1/2005 | Williams et al. |
| 6,867,247 B2 | 3/2005 | Williams et al. |
| 6,884,428 B2 | 4/2005 | Binette et al. |
| 6,932,834 B2 | 8/2005 | Lizardi et al. |
| 6,972,027 B2 | 12/2005 | Fallin et al. |
| 7,153,312 B1 | 12/2006 | Torrie et al. |
| 7,163,563 B2 | 1/2007 | Schwartz et al. |
| 7,588,587 B2 * | 9/2009 | Barbieri et al. ............... 606/232 |
| 7,608,098 B1 | 10/2009 | Stone et al. |
| 2002/0068930 A1 | 6/2002 | Tasto et al. |
| 2002/0169477 A1 | 11/2002 | Demopulos et al. |
| 2003/0078600 A1 | 4/2003 | O'Quinn et al. |
| 2003/0097148 A1 | 5/2003 | Valimaa et al. |
| 2003/0100859 A1 | 5/2003 | Henderson et al. |
| 2004/0064081 A1 | 4/2004 | Stanish |
| 2004/0093032 A1 | 5/2004 | Sinnott et al. |
| 2004/0230195 A1 | 11/2004 | Kaikkonen et al. |
| 2004/0260343 A1 | 12/2004 | Leclair |
| 2005/0033363 A1 | 2/2005 | Bojarski et al. |
| 2005/0234549 A1 | 10/2005 | Kladakis et al. |
| 2005/0246023 A1 | 11/2005 | Yeung |
| 2005/0271704 A1 | 12/2005 | Tu et al. |
| 2006/0089646 A1 | 4/2006 | Bonutti |
| 2006/0100627 A1 | 5/2006 | Stone et al. |
| 2006/0189993 A1 | 8/2006 | Stone |
| 2006/0190042 A1 | 8/2006 | Stone et al. |
| 2006/0247600 A1 | 11/2006 | Yeung et al. |
| 2006/0247642 A1 | 11/2006 | Stone et al. |
| 2006/0280768 A1 | 12/2006 | Hwang et al. |
| 2006/0282085 A1 | 12/2006 | Stone et al. |
| 2007/0067025 A1 | 3/2007 | Schwartz |
| 2007/0185532 A1 | 8/2007 | Stone et al. |
| 2008/0027446 A1 | 1/2008 | Stone et al. |
| 2008/0033487 A1 | 2/2008 | Schwartz et al. |
| 2008/0065114 A1 | 3/2008 | Stone et al. |
| 2008/0082128 A1 | 4/2008 | Stone |
| 2008/0132932 A1 | 6/2008 | Hoeppner et al. |
| 2008/0140092 A1 | 6/2008 | Stone et al. |
| 2008/0140093 A1 | 6/2008 | Stone et al. |
| 2008/0146918 A1 * | 6/2008 | Magnin et al. ............... 600/437 |
| 2008/0255613 A1 | 10/2008 | Kaiser et al. |
| 2008/0312689 A1 | 12/2008 | Denham et al. |
| 2009/0018561 A1 | 1/2009 | Schwartz et al. |
| 2010/0036389 A1 | 2/2010 | Schwartz et al. |

FOREIGN PATENT DOCUMENTS

| | | |
|---|---|---|
| CA | 2168835 | 8/1996 |
| JP | 03-178652 | 8/1991 |
| JP | 2004-000540 | 1/2004 |
| WO | 93/15694 | 8/1993 |
| WO | 97/32551 | 9/1997 |
| WO | 99/21510 | 5/1999 |
| WO | 00/36997 | 6/2000 |
| WO | 03/007784 | 1/2003 |
| WO | 03063713 A1 | 8/2003 |
| WO | 2005104992 | 11/2005 |

OTHER PUBLICATIONS

Amoczky et aL, J. of Bone and Joint Surgery, Meniscal Repair Using an Exogenous Fibrin Clot, vol. 70A(8), 1988, pp. 1200-1217.

Fox et al, J. of Arthroscopic and Related Surgery, Treytination of Incomplegte Meniscal Tears,9(4), 1993, pp. 451-455.

Okuda et aL, J of Arthroscopic and Related Surgery, Meniscal Rasping for Repair of Meniscal Tear in the Avascular Zone, vol. 15(3),1999, pp. 281-286.

O'Meara, p., Orthopaedic Review, The Basic Science of Meniscus Repair, Jun. 1993, pp. 681-686.

Sgaglione et at., J. of Arthroscopic and Related Surgery, Current Concpets in Meniscus Surgery Resection to Replacement, vol. 19(10), 2003, pp. 161-188.

Zhang et at., Am. J. of Sports Medidne, Repairs by Trephination and Suturing of Longitudinal Injuries in the AvascularArea of the Meniscus in Goats, vol. 23(1), 1995, pp. 35-41.

Smith & Nephew Technique Plus Illustrated Guide—Meniscal Repair with the FasT-Fix Suture System.

Supplementary European Search Report issued on Jul. 28, 2008 in connection with corresponding European Application No. EP 05 73 9944.

U.S. Appl. No. 10/983,236.
U.S. Appl. No. 10/984,624.

* cited by examiner

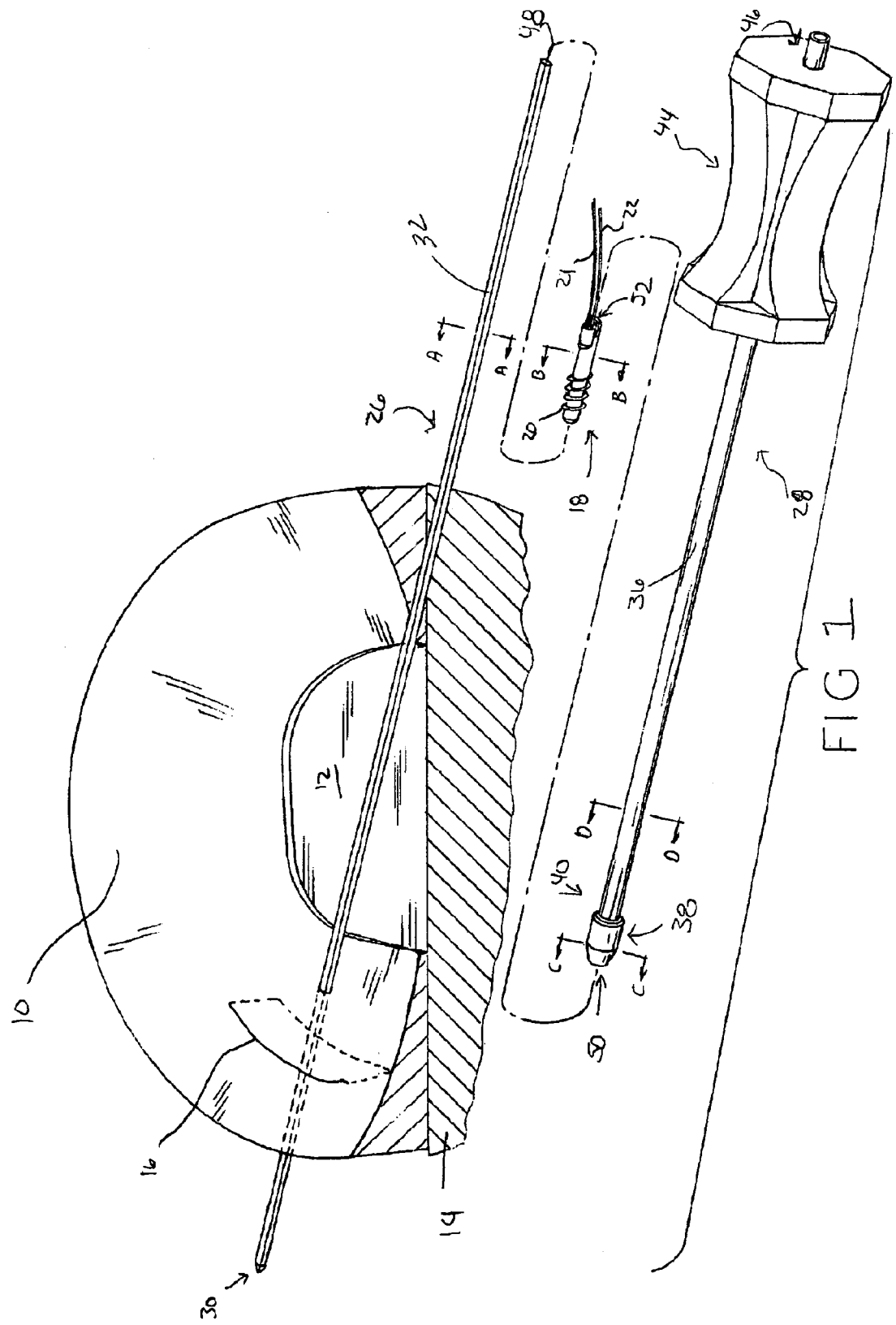

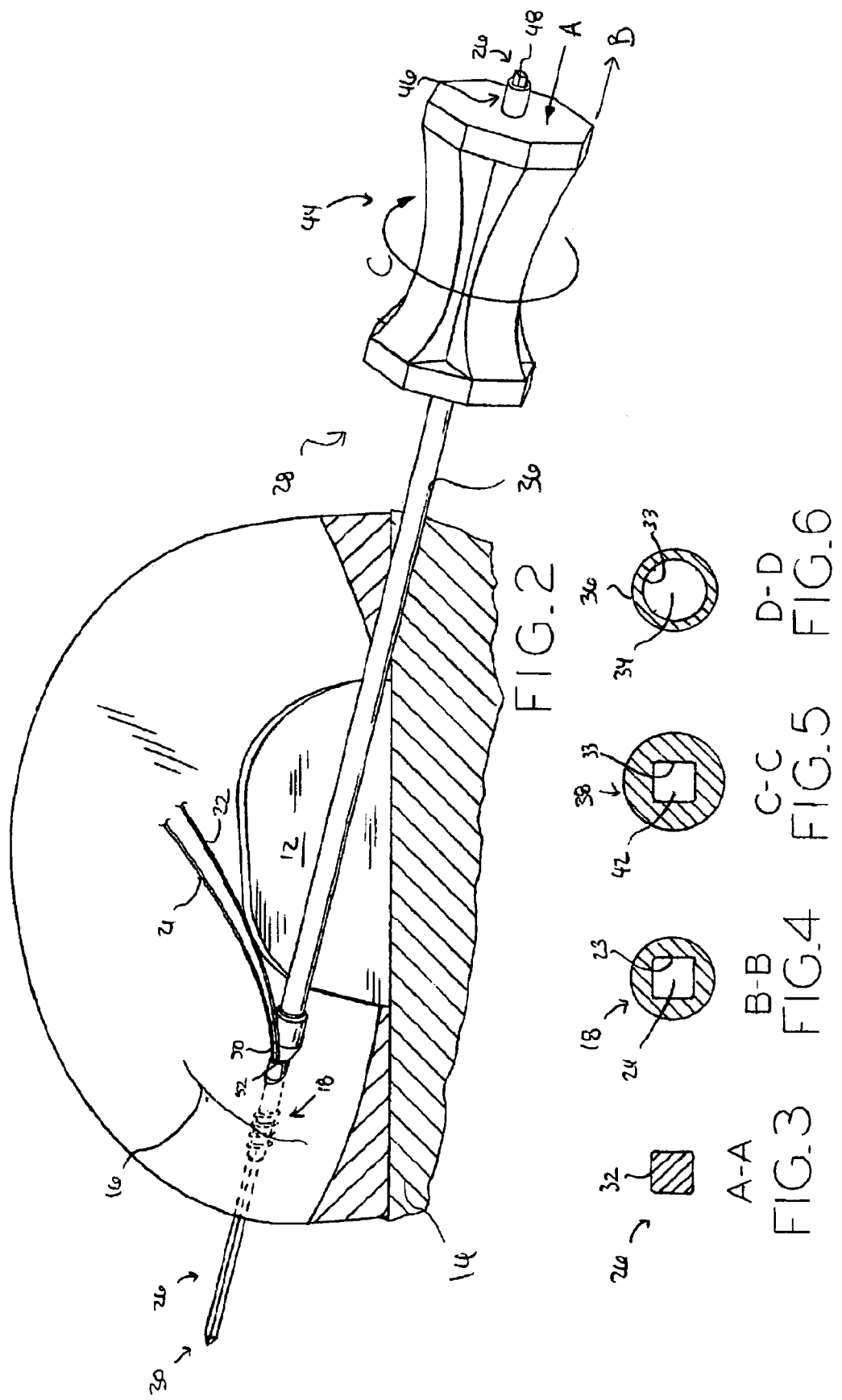

INSERTION SYSTEM FOR IMPLANTING A MEDICAL DEVICE AND SURGICAL METHODS

CROSS-REFERENCE TO RELATED APPLICATIONS

The present application is a national phase entry under 35 U.S.C. §371 of International Application No. PCT/US2007/075237 filed Aug. 6, 2007, published in English, which claims priority from U.S. Provisional Patent Application No. 60/821,593 filed Aug. 7, 2006, all of which are incorporated herein by reference.

BACKGROUND OF THE INVENTION

1. Field of the Invention

The present invention relates to an insertion system for implanting a medical device and to surgical methods for utilizing the same.

2. Description of the Related Art

Orthopedic surgeries are commonly performed to repair and replace damaged bone and tissue in the human body. To perform orthopedic surgery, a surgeon may create an incision and, if necessary, may retract the surrounding tissue to provide the necessary visual and physical access to the damaged bone and tissue. Once the incision is made and the tissue retracted, the surgeon will perform the necessary repair or replacement procedures. For example, if the meniscus of the knee is damaged the surgeon may perform a meniscectomy, i.e., remove a portion of a meniscus in the knee.

While surgical procedures requiring exposure of the damaged bone and tissue are effective, healing time for the patient may be greatly reduced if the surgery is performed using minimally invasive or arthroscopic techniques. These techniques allow the surgeon to make a small incision and perform the entire surgery therethrough. To perform surgery in this manner, the surgeon may utilize cannulated devices and other specially designed tools. While these procedures are effective, the insertion and manipulation of medical devices through the small incision is difficult. For example, certain medical devices for repairing tissue are extremely small and may require accurate placement to achieve optimum results.

SUMMARY OF THE INVENTION

The present invention relates to an insertion system for medical devices and to surgical methods for the implantation of the same. In one embodiment, the implantation system includes a guide wire and an insertion tool. The insertion tool includes a longitudinal bore extending therethrough for receipt of the guide wire. A portion of the longitudinal bore of the insertion tool mates with the outer surface of the guide wire to rotationally lock the insertion tool and the guide wire. Additionally, the medical device to be inserted includes a longitudinal bore for receipt of the guide wire. Similarly, at least a portion of the longitudinal bore of the medical device may also mate with the outer surface of the guide wire to rotationally lock the medical device and the guide wire. The rotational locks allow for rotation of the insertion tool to result in corresponding rotation of the medical device via rotation of the guide wire. Additionally, in another embodiment, the insertion tool includes features which allow for filament management, i.e., reduce or prevent filament entanglement during medical device insertion. In a further embodiment, the insertion system further includes a needle having an eyelet for receiving and positioning filaments attached to the medical device.

Advantageously, the present insertion system allows for the insertion of the medical device without any direct mechanical connection between the medical device and the insertion tool. This allows the surgeon to easily maneuver the insertion tool without correspondingly altering the position of the medical device, i.e., the insertion tool and the medical device are independently axially movable along the guide wire. Additionally, by utilizing the guide wire to rotate the medical device, rotational force may be provided along a greater length of the medical device instead of at a single point connected to the insertion tool.

In one form thereof, the present invention provides an insertion system for a medical device comprising a guide wire having an outer surface; a medical device having a first inner surface, the first inner surface defining a first bore adapted for receiving the guide wire therethrough; whereby the guide wire and the medical device are rotationally locked when the guide wire is received through the first bore; and an insertion tool having a second inner surface, the second inner surface defining a second bore adapted for receiving the guide wire therethrough, whereby the guide wire and the insertion tool are rotationally locked when the guide wire is received in the second bore.

In another form thereof, the present invention provides An insertion system for a medical device comprising: a guide wire having an outer surface; a medical device having an inner surface defining a bore extending therethrough, the bore adapted to receive the guide wire therein, wherein at least a portion of the outer surface of the guide wire and at least portion of the inner surface of the medical device are in mating engagement when the guide wire is received in the bore; and an insertion tool having an inner surface defining a longitudinal bore extending therethrough, the longitudinal bore adapted to receive the guide wire therein, wherein at least a portion of the inner surface of the longitudinal bore and at least of portion of the outer surface of the guide wire are in mating engagement when the guide wire is received in the longitudinal bore.

BRIEF DESCRIPTION OF THE DRAWINGS

The above-mentioned and other features and advantages of this invention, and the manner of attaining them, will become more apparent and the invention itself will be better understood by reference to the following description of an embodiment of the invention taken in conjunction with the accompanying drawings, wherein:

FIG. 1 is a fragmentary prospective view of a meniscus and other knee anatomy and an exploded view of the insertion system of the present application;

FIG. 2 is a fragmentary prospective view of a meniscus and other knee anatomy including the insertion system of FIG. 1;

FIG. 3 is a cross-sectional view along line A-A of FIG. 1;

FIG. 4 is a cross-sectional view along line B-B of FIG. 1;

FIG. 5 is a cross-sectional view along line C-C of FIG. 1;

FIG. 6 is a cross-sectional view along line D-D of FIG. 1;

Figure 7:
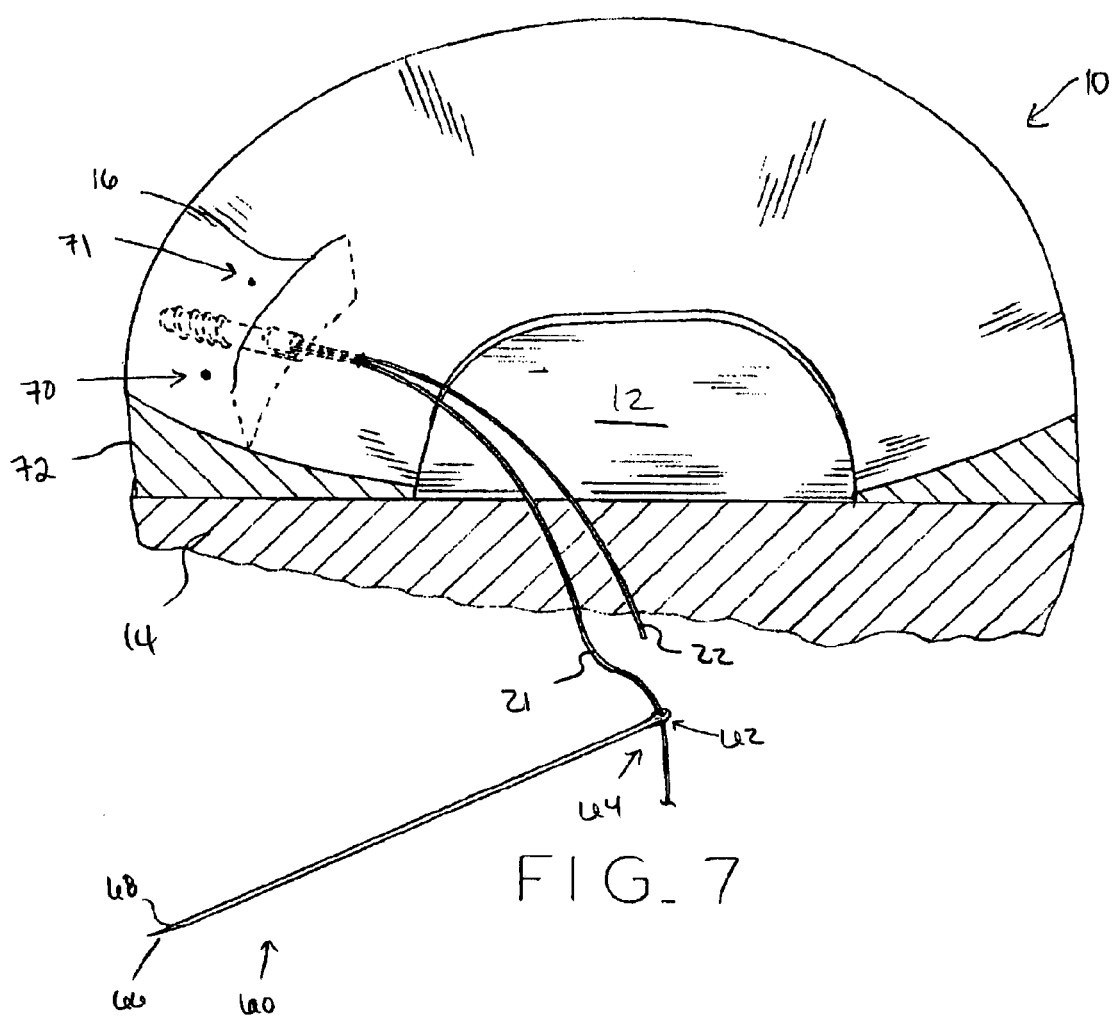
FIG. 7 is a fragmentary prospective view of a meniscus and other knee anatomy including a needle.

The exemplification set out herein illustrates a preferred embodiment of the invention and such exemplification is not to be construed as limiting the scope of the invention in any manner.

DETAILED DESCRIPTION

As shown in FIG. 1, meniscus 10 is located on tibial plateau 12 of tibia 14. Meniscus 10 includes tear 16 extending partially therethrough. To transfer blood, biological factors, and cells from a vascular region of tissue to tear 16 and thereby effect healing, medical device 18 may be used. Medical device 18 is the subject of U.S. patent application Ser. No. 11/462,728 entitled MEDICAL DEVICE FOR REPAIR OF TISSUE AND METHOD FOR IMPLANTATION AND FIXATION filed on even date herewith, the entire disclosure of which is expressly incorporated by reference herein. While medical device 18 and the insertion system of the present application are described and depicted herein with specific reference to a knee and fixation of a tear in a meniscus, medical device 18 and the insertion system of the present application may be used in any situation where diseased or damaged tissue or bone exists. Medical device 18, shown in FIG. 1, includes threads 20 for retaining medical device 18 in the proper position within meniscus 10 and filaments 21, 22 for securing tissue, e.g., the opposing planes of tear 16, in the desired position. Additionally, medical device 18 includes inner surface 23 defining longitudinal bore 24, shown in FIG. 4, extending therethrough.

The insertion system of the present application may be used to insert medical device 18 into tissue, such as meniscus 10. The insertion system includes guide wire 26 and insertion tool 28. Guide wire 26 may include sharpened tip 30 to facilitate insertion of guide wire 26 into tissue. As shown in FIG. 3, guide wire 26 has a square cross-section formed by outer surface 32, shown in FIG. 3. While the cross-section of guide wire 26 formed by outer surface 32 is depicted and described herein as square, guide wire 26 may have any non-circular cross-sectional geometry. Further, guide wire 26 and insertion tool 28 may be made of a flexible material, such as Nitinol.

Insertion tool 28 includes inner surface 33 defining longitudinal bore 34, shown in FIG. 6, extending through shaft portion 36, shown in FIGS. 1 and 2, having a round cross-section. The cross-section of longitudinal bore 34 may have any geometric configuration. In one embodiment, the cross-section of longitudinal bore 34 is square and made slightly larger than the cross-section of guide wire 26 to facilitate mating engagement of inner surface 33 of bore 34 and outer surface 32 of guide wire 26. Further, insertion tool 28 includes tip portion 38 at distal end 40, shown in FIG. 1, thereof. Tip portion 38 of insertion tool 28 includes interior bore 42, shown in FIG. 5, defined by inner surface 33 extending longitudinally therethrough and having a square cross-section slightly larger than the cross-section of outer surface 32 of guide wire 26. This size and shape of interior bore 42 allows for mating engagement of inner surface 33 of tip portion 38 of insertion tool 28 and outer surface 32 of guide wire 26. Handle 44 is located adjacent proximal end 46 of shaft portion 36 and facilitates the rotation and gripping of insertion tool 28 by a surgeon.

To insert medical device 18, guide wire 26 is first inserted through meniscus 10. Guide wire 26 should be positioned coaxially with the desired implantation line of medical device 18, which, in the case of FIG. 1, follows a path through the plane of tear 16. Longitudinal bore 24 of medical device 18, shown in FIG. 4, has a square cross-section slightly larger than the cross-section of outer surface 32 of guide wire 26. The size and shape of longitudinal bore 24 allow for mating engagement of inner surface 23 of medical device 18 and outer surface 32 of guide wire 26. Once guide wire 26 is properly positioned at least partially in meniscus 10, longitudinal bore 24 of medical device 18 is aligned with end 48 of guide wire 26. Once aligned, medical device 18 may be slid onto guide wire 26 with inner surface 23 of medical device 18 and outer surface 32 of guide wire 26 in mating sliding engagement and rotationally locking medical device 18 and guide wire 26. In the same manner as medical device 18, interior bore 42 of tip portion 38 of insertion tool 28 is aligned with end 48 of guide wire 26. Once aligned, insertion tool 28 is slid onto guide wire 26 and, as insertion tool 28 is advanced toward the patient's body, guide wire 26 may be allowed to extend from proximal end 46 of insertion tool 28, as shown in FIG. 2. In this position, at least a portion of inner surface 33 of insertion tool 28 and outer surface 32 of guide wire 26 are in mating engagement, rotationally locking insertion tool 28 and guide wire 26.

Once the insertion system is assembled as shown FIG. 2, with guide wire 26 properly positioned at least partially within meniscus 10 and medical device 18 and insertion tool 28, respectively, positioned on guide wire 26, insertion tool 28 is advanced toward the patient until distal end 50 of tip portion 38 of insertion tool 28 contacts proximal end 52 of medical device 18. In this position, additional axial movement of insertion tool 28 by the surgeon along guide wire 26 in the direction of Arrow A will push medical device 18 forward toward tear 16. As threads 20 of medical device 18 encounter meniscus 10, insertion tool 28 may be rotated by the surgeon to facilitate insertion of medical device 18 into meniscus 10. Due to the cross-section of outer surface 32 of guide wire 26 corresponding to the cross-sections of bores 24, 42 of medical device 18 and tip portion 38, respectively, as described in detail above, rotation of insertion tool 28 in the direction of Arrow C will result in corresponding rotation of guide wire 26 and medical device 18. The surgeon can utilize the appropriate combination of axial movement and rotation to properly position medical device 18 within meniscus 10. In one embodiment, medical device 18 lacks threads 20. To insert this embodiment of medial device 18, only axial movement of insertion tool 28 is required.

Once medical device 18 is positioned in its desired location in meniscus 10, as shown in FIG. 2, insertion tool 28 may be removed from guide wire 26 by sliding insertion tool 28 axially along guide wire 26 in the direction indicated by Arrow B, as shown in FIG. 2. Once insertion tool 28 is removed, guide wire 26 may be removed from meniscus 10 by pulling guide wire 26 in the direction of Arrow A or, alternatively, by pulling guide wire 26 in the direction indicated by Arrow B (FIG. 2).

In one exemplary embodiment, shown in FIG. 7, the insertion system further includes needle 60. Needle 60 is utilized to position filaments 21, 22 of medical device 18 within meniscus 10 to close tear 16 by fixating the planes of tear 16 into mating engagement. In another embodiment, insertion tool 28 contains features to maintain filaments 21, 22 and needle 60, i.e., prevent rotation or entanglement of filaments 21, 22 and needle 60, during medical device insertion. Needle 60 includes eyelet 62 at proximal end 64. In an exemplary embodiment, needle 60 further includes sharpened tip 66 at distal end 68 to facilitate insertion. To position filaments 21, 22, needle 60 is inserted into the patient's body using known minimally invasive or arthroscopic techniques. Either before or after needle 60 is inserted into the patient's body, filament 21 is inserted through eyelet 62 and distal end 68 of needle 60 is inserted into meniscus 10 at insertion point 70. Insertion point 70 may be any point in meniscus 10 through which a surgeon desires to place filament 21. Needle 60 may then be pushed through outer wall 72 of meniscus 10 and is then removed from meniscus 10. Once needle 60 is removed from meniscus 10, filament 21 may be removed from eyelet 62 of needle 60 and needle 60 may be completely removed from the patient's body. Depending on the surgical technique utilized, removal of needle 60 from the patient's body may require an additional incision adjacent outer wall 72 of meniscus 10.

Figure 8:
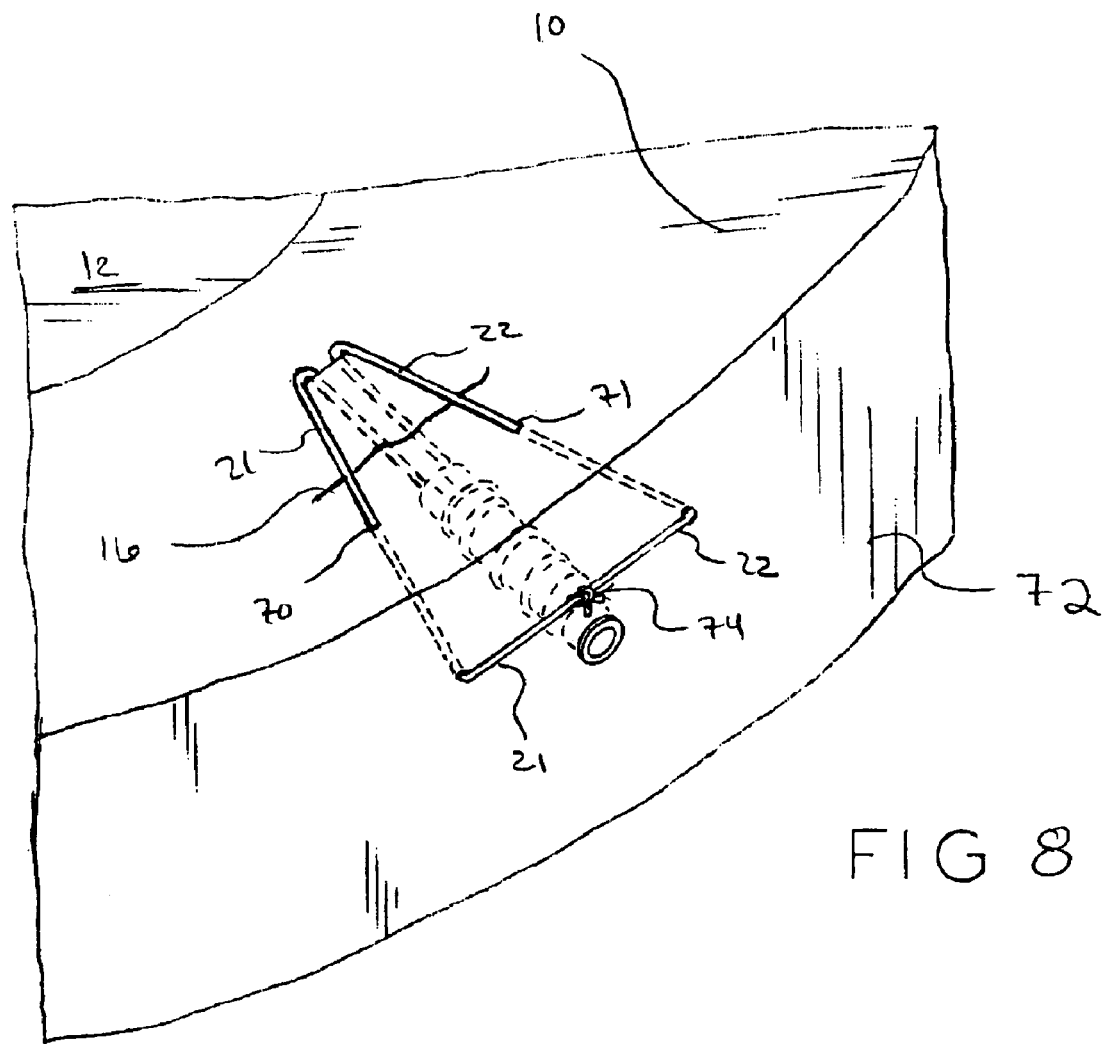
FIG. 8 is a perspective view of the medical device implanted in a meniscus.

To position filament 22, needle 60 is reinserted using known minimally invasive or arthroscopic techniques and filament 22 is then inserted through eyelet 62 of needle 60. Distal end 68 of needle 60 is then inserted into meniscus 10 at insertion point 71. Similarly, insertion point 71 may be any point in meniscus 10 through which a surgeon desires to place filament 22. Needle 60 may then be pushed through outer wall 72 of meniscus 10 and removed from meniscus 10. Once needle 60 is removed from meniscus 10, needle 60 may be completely removed from the patient's body and filament 22 removed from eyelet 62 of needle 60. In another exemplary embodiment, a pair of needles 60 are used, one for filament 21 and one for filament 22, allowing the surgeon to position filaments 21, 22 substantially simultaneously. Filaments 21, 22 may then be secured to one another by any known method, such as by knot 74, shown in FIG. 8. Additionally, other methods of securing filaments 21, 22 together may be used, such as those methods disclosed in the above-incorporated patent application entitled MEDICAL DEVICE FOR REPAIR OF TISSUE AND METHOD FOR IMPLANTATION AND FIXATION. Once secured, the ends of filaments 21, 22 may be trimmed and the excess removed.

What is claimed is:

1. An insertion system for an implantable medical device comprising:
   a guide wire having an outer surface;
   an implantable medical device having a first inner surface, said first inner surface defining a first bore adapted for receiving said guide wire therethrough, whereby said guide wire and said implantable medical device are rotationally locked when said guide wire is received through said first bore; and
   an insertion tool having a second inner surface, said second inner surface defining a second bore adapted for receiving said guide wire therethrough, whereby said guide wire and said insertion tool are rotationally locked when said guide wire is received in said second bore;
   wherein said implantable medical device and said insertion tool are independently axially moveable along said guide wire.

2. The insertion system of claim 1, wherein said implantable medical device and said insertion tool are both axially displaceable relative to said guide wire when said guide wire is received in said first and second bores.

3. The insertion system of claim 1, wherein said implantable medical device further includes a filament connected thereto.

4. The insertion system of claim 3, further comprising a needle, said needle having an eyelet adapted for receipt of said filament therethrough.

5. The insertion system of claim 1, wherein the guide wire further includes a tip, and wherein said outer surface has a uniform cross-section.

6. The insertion system of claim 1, wherein said first bore includes a first cross-section and said second bore includes a second cross-section that is substantially identical to said first cross-section.

7. An insertion system for an implantable medical device comprising:
   a guide wire having an outer surface;
   an implantable medical device having an inner surface defining a bore extending therethrough, said bore adapted to receive said guide wire therein, wherein at least a portion of said outer surface of said guide wire and at least a portion of said inner surface of said implantable medical device are in rotational mating engagement when said guide wire is received in said bore; and
   an insertion tool having an inner surface defining a longitudinal bore extending therethrough, said longitudinal bore adapted to receive said guide wire therein, wherein at least a portion of said inner surface of said longitudinal bore and at least a portion of said outer surface of said guide wire are in rotational mating engagement when said guide wire is received in said longitudinal bore;
   wherein said implantable medical device and said insertion tool are independently axially moveable along said guide wire.

8. The insertion system of claim 7, wherein the mating engagement of said implantable medical device and said insertion tool with said guide wire allows axial movement of said implantable medical device and said insertion tool along said guide wire.

9. The insertion system of claim 7, further comprising a needle having an eyelet for receiving a filament, wherein said filament is attached to said implantable medical device.

10. The insertion system of claim 7, wherein the cross-sections of said outer surface of said guide wire, at least a portion of said inner surface of said implantable medical device, and at least a portion of said inner surface of said insertion tool are non-circular.

11. The insertion system of claim 7, wherein the guide wire further includes a tip, and wherein said outer surface has a uniform cross-section.

12. The insertion system of claim 7, wherein said bore of said implantable medical device includes a first cross-section and said longitudinal bore of said insertion tool includes a second cross-section that is substantially identical to said first cross-section.

13. An insertion system for an implantable medical device comprising:
   a guide wire having an outer surface;
   an implantable medical device having a first inner surface, said first inner surface defining a first bore adapted for receiving said guide wire therethrough, whereby said guide wire and said implantable medical device are rotationally locked when said guide wire is received through said first bore; and
   an insertion tool having a second inner surface, said second inner surface defining a second bore adapted for receiving said guide wire therethrough, whereby said guide wire and said insertion tool are rotationally locked when said guide wire is received in said second bore;
   wherein there is no direct rotational mechanical connection between said implantable medical device and said insertion tool.

14. An insertion system for an implantable medical device comprising:
   a guide wire having an outer surface and a tip, said outer surface including a uniform cross-section;
   an implantable medical device having a first inner surface, said first inner surface defining a first bore adapted for receiving said guide wire therethrough, whereby said guide wire and said implantable medical device are rotationally locked when said guide wire is received through said first bore; and
   an insertion tool having a second inner surface, said second inner surface defining a second bore adapted for receiving said guide wire therethrough, whereby said guide wire and said insertion tool are rotationally locked when said guide wire is received in said second bore.

* * * * *